*(12)* United States Patent
Kwon et al.

(10) Patent No.: US 6,851,300 B2
(45) Date of Patent: Feb. 8, 2005

(54) APPARATUS FOR DETERMINING RESIDUAL STRESS, METHOD FOR DETERMINING RESIDUAL STRESS DATA USING IT, RESIDUAL STRESS DETERMINING METHOD USING IT AND RECORDING MEDIUM THEREOF

(75) Inventors: Dongil Kwon, Seoul (KR); Yunhee Lee, Kyungsangbuk-do (KR); Dongil Son, Seoul (KR)

(73) Assignee: Frontics Inc. (KR)

( * ) Notice: Subject to any disclaimer, the term of this patent is extended or adjusted under 35 U.S.C. 154(b) by 28 days.

(21) Appl. No.: 10/404,816

(22) Filed: Apr. 1, 2003

(65) Prior Publication Data

US 2003/0217591 A1 Nov. 27, 2003

(30) Foreign Application Priority Data

Apr. 4, 2002 (KR) .............................. 10-2002-0018521

(51) Int. Cl.$^7$ ................................................ G01N 3/00
(52) U.S. Cl. ............................................................ 73/85
(58) Field of Search ............................... 73/81, 85, 78, 73/83

(56) References Cited

U.S. PATENT DOCUMENTS

| | | | | |
|---|---|---|---|---|
| 4,856,326 A | * | 8/1989 | Tsukamoto | 73/150 A |
| 5,616,857 A | * | 4/1997 | Merck et al. | 73/82 |
| 6,142,010 A | * | 11/2000 | Merck et al. | 73/81 |
| 6,247,355 B1 | * | 6/2001 | Suresh et al. | 73/82 |
| 6,247,356 B1 | * | 6/2001 | Merck et al. | 73/82 |
| 6,718,820 B2 | * | 4/2004 | Kwon et al. | 73/81 |

OTHER PUBLICATIONS

A. Bolshakov et al., "Influences of stress on the meansurement of mechanical properties using nanoindentation: Part II. Finite element simulations", Journal of Materials Research, vol. 11, No. 3, Mar. 1996, pp. 760–768.

C.L. Eriksson et al., "Strain–hardening and residual stress effects in plastic zones around indentations", Materials Science and Engineering A00 (2002), pp. 1–11.

Yun–Hee Lee et al., "Residual stresses in DLC/Si and Au/SI systems: Application of a stress–relaxation model to the nanoindentation technique", Journal of Materials Research, vol. 17, No. 4, Apr. 2002, pp. 901–906.

S. Suresh et al., "A new method for estimating residual stresses by instrumented sharp indentation", Acta mater., vol. 46, No. 16, 1998, pp. 5755–5767.

(List continued on next page.)

*Primary Examiner*—Max Noori
(74) *Attorney, Agent, or Firm*—Harness, Dickey & Pierce, P.L.C.

(57) ABSTRACT

Disclosed herein is an apparatus for measuring residual stress, methods of measuring residual stress data and residual stress using the apparatus, and a recording medium for storing software of the residual stress measuring method. The present invention is advantageous for evaluation of a mechanical material property and is non-destructive. Further, the present invention is widely applied to fields ranging from a microscopic area, such as a thin film or micro device, to a large-sized structure, and is not influenced by a microstructure by controlling the range of an applied load. Further, the measuring apparatus of the present invention is minimized in its volume to be easily attached to an actual structure. Further, in the present invention, various attaching devices are employed, thus enabling the apparatus to be attached to various materials regardless of the size and type of object materials to measure residual stress. Further, the measuring apparatus of the present invention is horizontally movable, so there is no need to move an apparatus body itself so as to take measurements at several positions of several materials. Further, the present invention does not require separate measurements for correcting experimental constants at the time of analyzing measured data.

18 Claims, 14 Drawing Sheets

OTHER PUBLICATIONS

T.Y. Tsui et al., "Influences of stress on the measurement of mechanical properties using nanoindentation: Part I. Experimental studies in an aluminum alloy", Journal of Materials Research, vol. 11, No. 3, Mar. 1996, pp. 752–759.

Audrey V. Zagrebelny et al., "Indentation of strained silicate–glass films on alumina substrates", Scripta Materialia, vol. 37, No. 12, 1997, pp. 1869–1875.

* cited by examiner

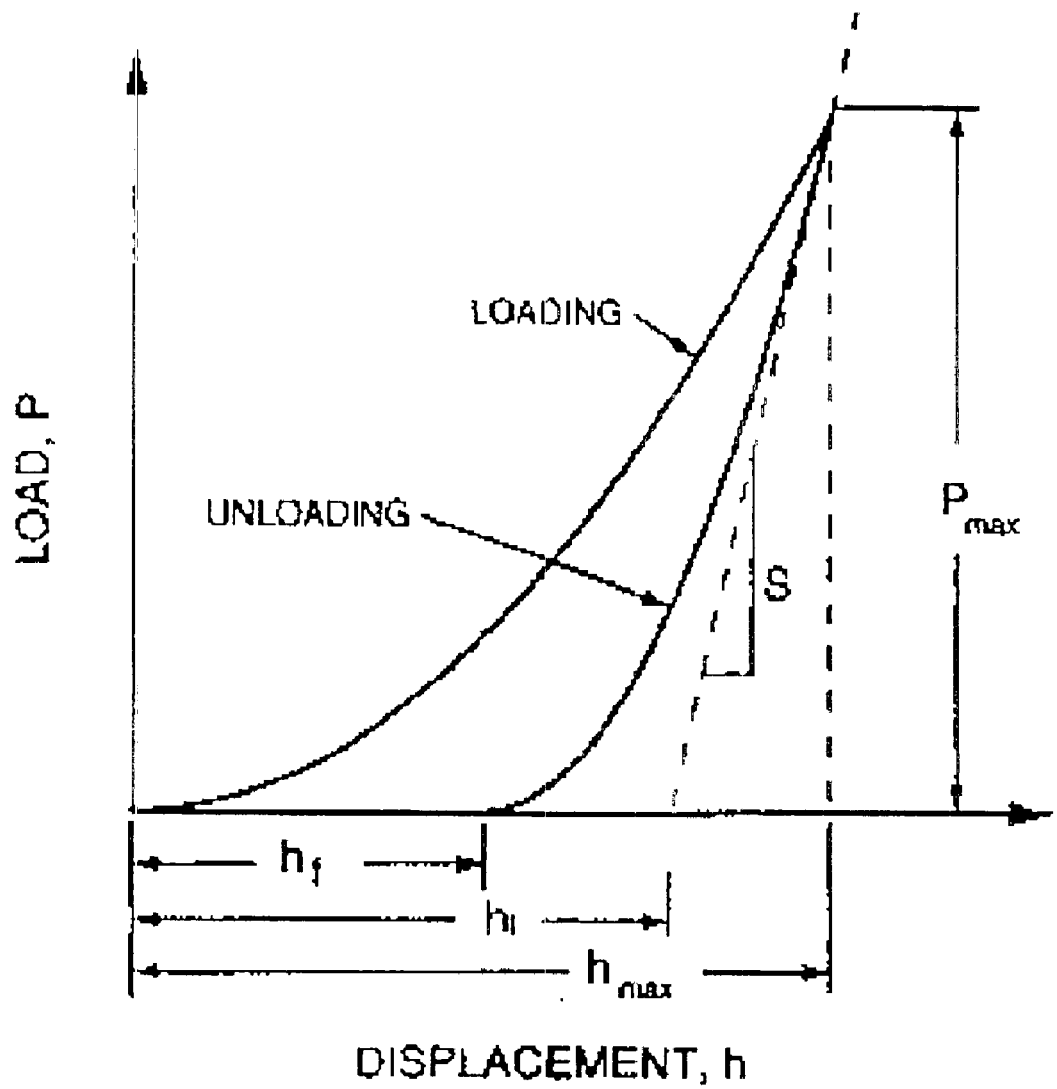

APPARATUS FOR DETERMINING RESIDUAL STRESS, METHOD FOR DETERMINING RESIDUAL STRESS DATA USING IT, RESIDUAL STRESS DETERMINING METHOD USING IT AND RECORDING MEDIUM THEREOF

BACKGROUND OF THE INVENTION

1. Field of the Invention

The present invention relates generally to an apparatus for measuring residual stress, methods of measuring residual stress data and residual stress using the apparatus, and a recording medium for storing software of the residual stress measuring method.

2. Description of the Prior Art

Residual stress generated due to the strain or thermal stress imposed on a material causes several problems, such as the deterioration of mechanical properties including the fatigue strength and destructive material property of a material and the like, and difficulty of post-processing. Especially, in the case of a thin film material rapidly increased in its use in recent times, it is reported that residual stress generated at a interface between different materials is an important factor influencing mechanical integrity of whole system. For bulk materials, the importance of residual stress generated during welding is well known.

Conventional methods of measuring residual stress are classified into two types: one is a mechanical stress relaxing method, such as hole drilling or saw cutting, and the other is a physical method, such as X-ray diffraction, Barkhausen magnetic noise measurement, ultrasonic techniques or neutron diffraction.

The mechanical stress relaxing method measures residual stress using a degree of strain of a material when a constraint factor is removed from the material and so the material is relaxed. Such mechanical stress relaxing method is advantageous in that it can quantitatively estimate residual stress without a comparison sample, while it is disadvantageous in that it must destroy the sample.

Of physical methods, X-ray diffraction is a method of measuring a distance between atoms and calculating a degree of strain using the distance. The Barkhausen magnetic noise measurement is a method of calculating the variation of Barkhausen noise which is one of magnetic field noises varying depending on residual stress.

Such physical methods have both an advantage of non-destructiveness, and a disadvantage of high sensitivity to the microstructure of a material, so it is impossible to apply the physical methods to an area on which a sudden variation of a microstructure, such as a welding part, exists (in this case, it is difficult to determine whether a measured result value is residual stress or variation of microstructure).

As described above, the conventional residual stress measuring methods are problematic in that they cannot compensate the stress relaxation during sampling from stressed structure, and they require a complicated and difficult process of material removal without additional damage.

SUMMARY OF THE INVENTION

Accordingly, the present invention has been made keeping in mind the above problems occurring in the prior art, and an object of the present invention is to provide an apparatus and method for measuring residual stress, which is advantageous in mechanical property evaluation and is non-destructive.

Another object of the present invention is to provide an apparatus and method for measuring residual stress, which is widely applied to fields ranging from a microscopic area, such as a thin film or micro device, to a large-sized structure, and is not influenced by a microstructure by controlling the range of an applied load.

A further object of the present invention is to provide an apparatus for measuring residual stress, which is minimized in its volume to be easily attached to an actual structure.

Still another object of the present invention is to provide an apparatus and method for measuring residual stress, in which various attaching devices are employed, thus enabling the apparatus to be attached to various materials regardless of the size and type of object materials to measure residual stress.

Still another object of the present invention is to provide an apparatus for measuring residual stress, which is horizontally movable, so there is no need to move a main body itself so as to take measurements at several positions of a material.

Still another object of the present invention is to provide an apparatus and method for measuring residual stress, which does not require separate measurements for correcting experimental constants at the time of analyzing measured data, thus reducing measurement costs and enabling residual stresses of parts, which were impossible to measure using other conventional measuring methods, to be measured.

In order to accomplish the above object, the present invention provides an apparatus for measuring residual stress, comprising a main body; a load applying device installed within the main body to generate a load applied to a material to be measured; a load sensor for continuously measuring variation of the load applied to the material by the load applying device; an indenter holder connected to the load applying device and coaxially driven together with the load sensor; an indenter provided with a first end coupled with the indenter holder and a second end coming into contact with the material to apply the load generated by the load applying device to the material; a displacement sensor for continuously measuring variation of an indentation depth according to indentation of the indenter; and an interface computer provided with a measurement program for measuring residual stress on the basis of values measured by the load sensor and the displacement sensor.

Preferably, the interface computer is provided with one or more control buttons for controlling the load applying device.

Preferably, the measurement program measures the variations of the load and the indentation depth by allowing the indenter to approach the material to apply the load to the material by an operation of any one of the control buttons and removing the applied load, and further calculates residual stress by continuously measuring the variations of the load and the indentation depth.

Preferably, the residual stress measuring apparatus further comprises an attaching device used to fix the material to be measured to the residual stress measuring apparatus, the attaching device being at least one of a magnet, a chain and a U-block.

Preferably, the residual stress measuring apparatus further comprises a horizontal moving device for horizontally moving the main body with the indenter attached thereto in at least one direction after the attaching device is fixed to the residual stress measuring apparatus.

Preferably, the horizontal moving device comprises a slider base connected to a base supporting the main body on an upper surface of the base and provided with a dovetail groove formed in an upper portion of the slider base; a slider disposed between the slider base and the main body to be slidably interlocked with the slider base in a dovetail shape; and a moving handle for horizontally moving the slider on the slider base in at least one direction.

Preferably, the indenter is formed in at least one shape of a cone and a square pyramid, and is integrated with the indenter holder.

In addition, the present invention provides a method of measuring residual stress data of a material using the residual stress measuring apparatus, comprising the steps of a) moving the indenter to a position where a residual stress experiment can be started to allow the indenter to approach the material; b) setting a movement speed and a movement distance of the indenter and applying the load to the material; c) vertically moving the indenter by the set movement depth of the indenter and then moving the indenter upward by a certain load removal ratio of the movement distance of the indenter; d) measuring an indentation depth and an indentation load of the indenter according to the vertical movement of the indenter, simultaneously with performance of steps b) and c); e) repeatedly performing the steps b), c) and d) a plurality of times; f) removing the indenter from the material; and g) calculating residual stress of the material.

Preferably, the step b) comprises the steps of b1) moving the indenter downward; and b2) stopping the downward movement of the indenter and moving the indenter upward by a distance set value if the indentation load is greater than or equal to a load set value, and continuously performing the step b1) if the indentation load is less than the load set value.

Preferably, the load set value is 0.01 to 2 kgf, and the distance set value is 0.1 to 30 μm.

Preferably, the step g) is performed before or after the step f) is executed.

Preferably, the step e) is performed in such a way that at least one of the movement speed of the indenter, the movement distance of the indenter and the load removal ratio can be varied in each experiment step.

In addition, the present invention provides a method of measuring residual stress of a material using the residual stress measuring apparatus, comprising the steps of a) moving the indenter downward to a position where an indentation experiment can be started, stopping the downward movement of the indenter and moving the indenter upward by a distance set value if an indentation load is greater than or equal to a load set value, and continuously moving the indenter downward, if the indentation load is less than the load set value; b) setting a movement speed and a movement distance of the indenter and applying the load to the material; c) vertically moving the indenter downward by the set movement distance of the indenter and then moving the indenter upward by a certain load removal ratio of the movement distance of the indenter; d) measuring an indentation depth and an indentation load of the indenter according to the vertical movement of the indenter through the steps b) and c); e) repeatedly performing the steps b), c) and d) a plurality of times; f) measuring residual stress of the material by comparing measurement equations of a reference sample and the measured material with each other; and g) removing the indenter from the material.

In addition, the present invention provides a recording medium for storing software of a method of measuring residual stress of a material using the residual stress measuring apparatus, comprising indenter approaching means for moving the indenter downward to a position where an indentation experiment can be started, stopping the downward movement of the indenter and moving the indenter upward by a distance set value if an indentation load is greater than or equal to a load set value, and continuously moving the indenter downward if the indentation load is less than the load set value; load applying means for setting a movement speed and a movement distance of the indenter and applying the load to the material; load removing means for vertically moving the indenter down by the set movement distance of the indenter and then moving the indenter upward by a certain load removal ratio of the movement distance of the indenter; measuring means for measuring an indentation depth and an indentation load of the indenter according to the vertical movement of the indenter through the load applying means and the load removing means; continuous measuring means for repeatedly performing operations of the load applying means, the load removing means and the measuring means a plurality of times; indenter removing means for removing the indenter from the material; and means for measuring residual stress of the material by comparing measurement equations of a reference sample and the measured material with each other.

Therefore, a continuous indentation measuring method is disclosed as a measuring method which is advantageous for mechanical property evaluation and is non-destructive. In such a continuous indentation measuring method, the strain of a material to an indentation load is represented with an indentation load versus displacement curve, in which the shape of the curve varies sensitively to residual stress.

Further, the continuous indentation measuring method is advantageous in that, since the range of an applied load is controlled, the method is widely applied to fields ranging from a microscopic area, such as a thin film or micro device, to a large-sized structure, and is not influenced by a microstructure, so the continuous indentation measuring method can be widely used as a new residual stress measuring method.

BRIEF DESCRIPTION OF THE DRAWINGS

The above and other objects, features and other advantages of the present invention will be more clearly understood from the following detailed description taken in conjunction with the accompanying drawings, in which:

FIG. 14 is a graph showing an indentation load versus displacement curve which is obtained through the residual stress measuring apparatus.

DESCRIPTION OF THE PREFERRED EMBODIMENTS

Hereinafter, the present invention will be described in detail with reference to the attached drawings. An apparatus for measuring residual stress, methods of measuring residual stress data and residual stress using the apparatus, and a recording medium for storing software of the residual stress measuring method using the residual stress measuring apparatus will be described in order. Thereafter, embodiments of the residual stress measuring method using a measurement program will be described in detail through equations.

1. Residual Stress Measuring Apparatus

Figure 1:
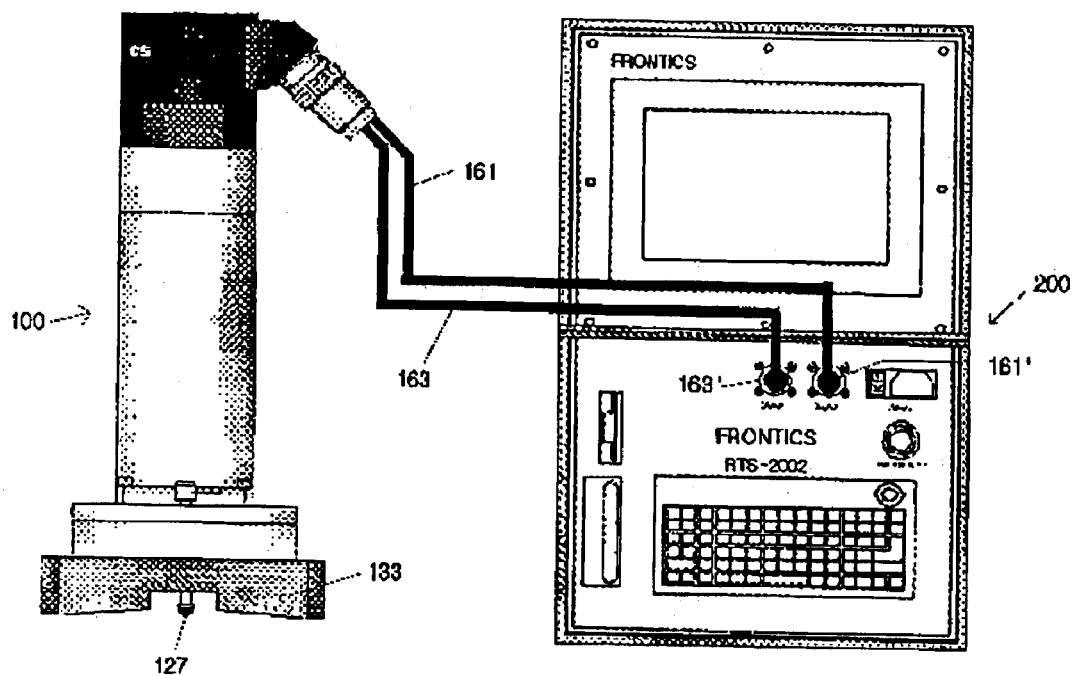
FIG. 1 is a view showing an entire construction of an apparatus for measuring residual stress according to an embodiment of the present invention.
Figure 4:
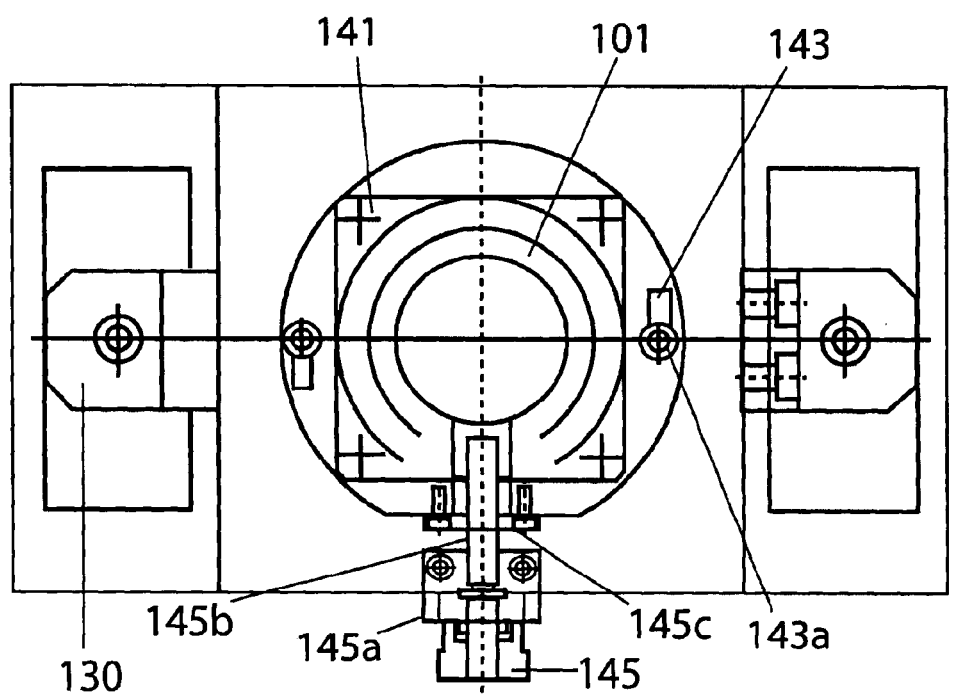
FIG. 4 is a partial plan view of the main body of FIG. 2.
Figure 5:
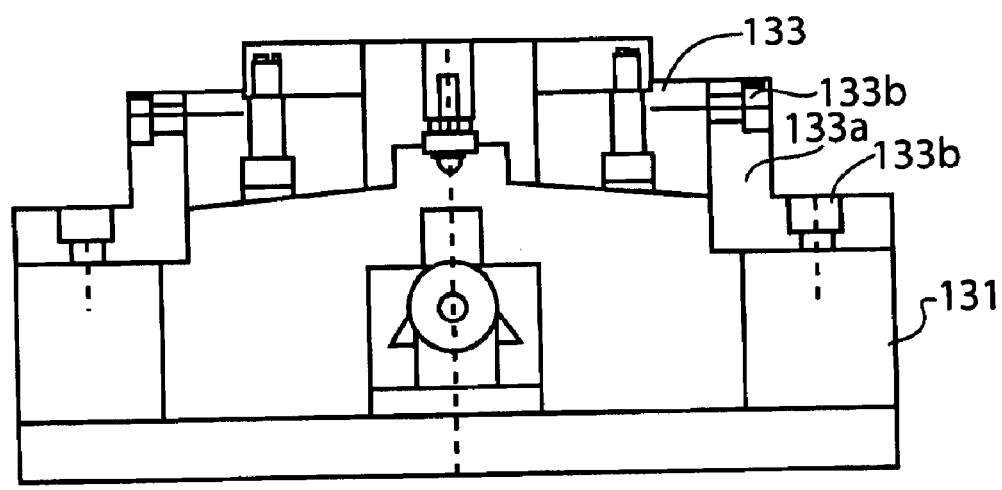
FIG. 5 is a partial sectional view showing a part of a lower portion of the main body of FIG. 2, a displacement sensor region and a load sensor region.

An embodiment of an apparatus for measuring residual stress is described with reference to FIGS. 1 to 5. FIG. 1 is a view showing an entire construction of a residual stress measuring apparatus according to an embodiment of the present invention, FIG. 2 is a front sectional view of a main body of the residual stress measuring apparatus shown in FIG. 1, FIG. 3 is a side sectional view of the main body of FIG. 2, FIG. 4 is a partial plan view of the main body of FIG. 2, and FIG. 5 is a partial sectional view showing a part of a lower portion of the main body of FIG. 2, a displacement sensor region and a load sensor region.

As shown in FIG. 1, the residual stress measuring apparatus of the present invention comprises a main body 100 and an interface computer 200 connected to the main body 100.

The main body 100 is a main part attached to a material to measure the residual stress of the material. In the interface computer 200, programs for controlling the operation of the main body 100 and analyzing data measured by a measuring means of the main body 100, and devices for converting signal values generated by the main body 100, are mounted.

Figure 2:
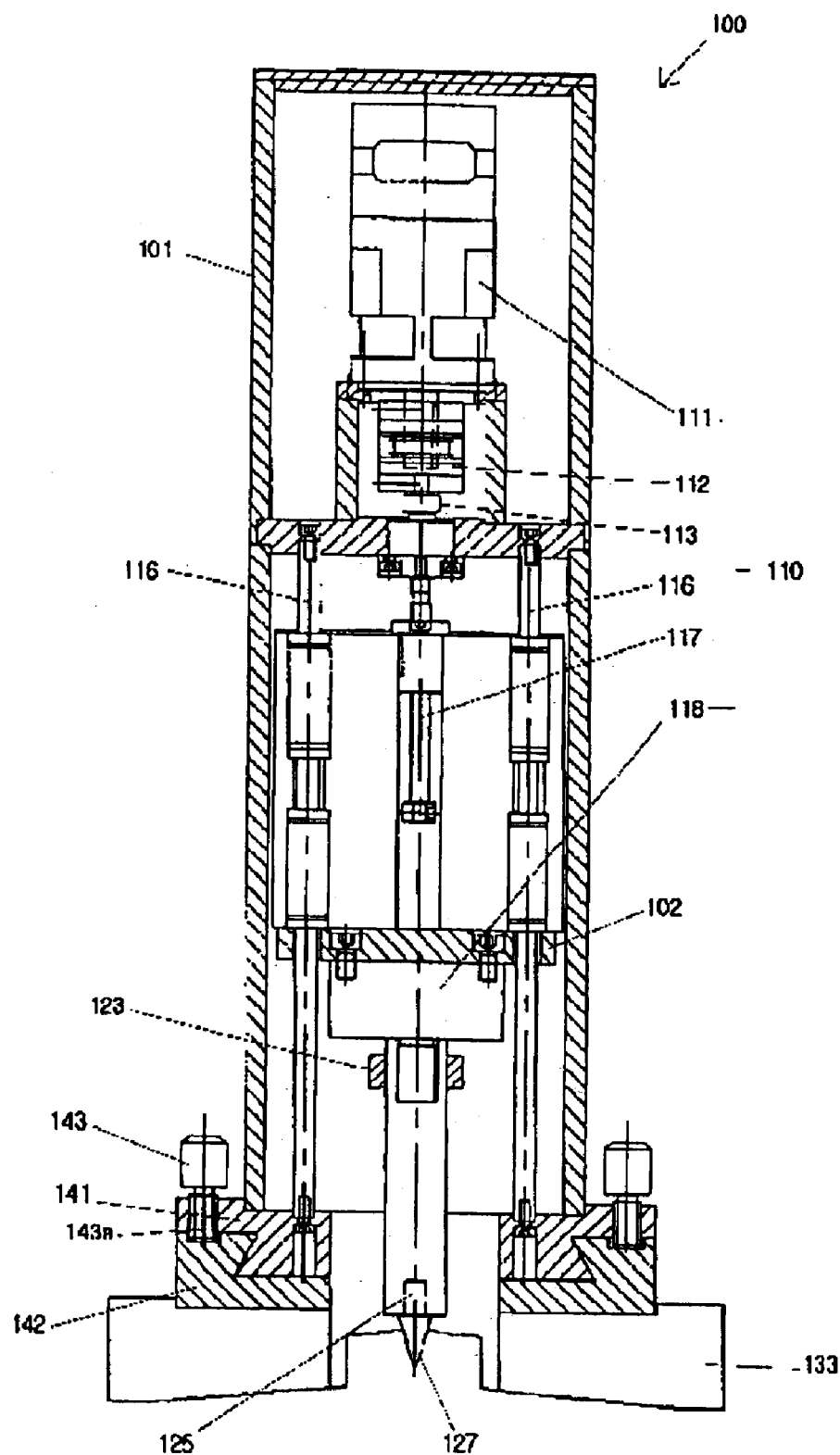
FIG. 2 is a front sectional view of a main body of the residual stress measuring apparatus shown in FIG. 1.
Figure 3:
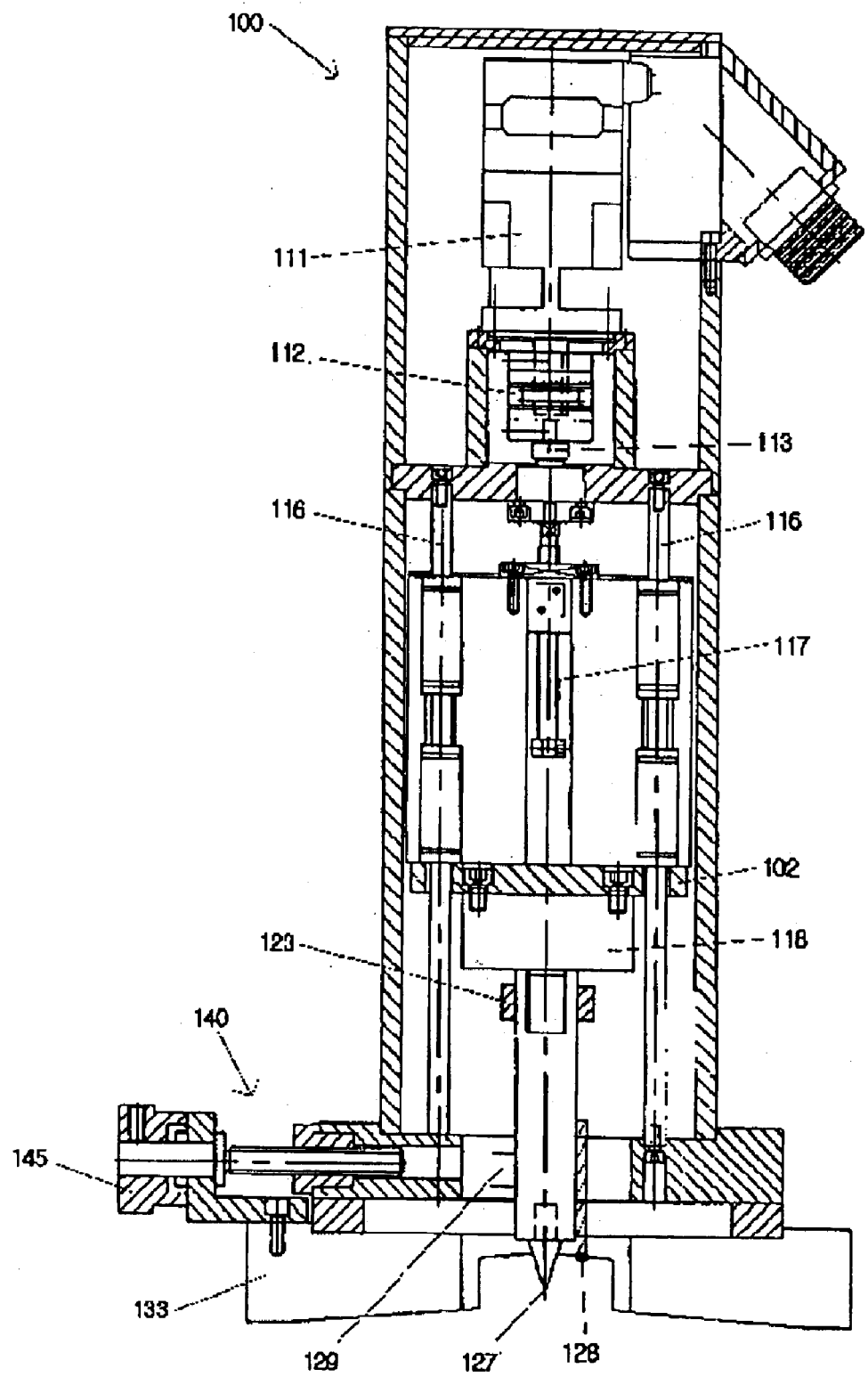
FIG. 3 is a side sectional view of the main body of FIG. 2.

As shown in FIGS. 2 and 3, the main body 100 comprises a frame 101, a load applying device 110, a body 102, a load sensor 123, an indenter holder 125, an indenter 127, a displacement sensor 128, a horizontal moving device 140, and connectors 161 and 163.

The frame 101 is formed in the shape of a cylinder to protect a plurality of parts included therein and to constitute an exterior shape of the residual stress measuring apparatus. In the embodiment, since the frame 101 accommodates the load applying device 110, the body 102, the load sensor 123 and a part of the indenter 127, the frame 101 is made of light aluminum alloy with high strength. Meanwhile, the weight of the frame 101 is low, so it is easy to carry the apparatus.

The load applying device 110 generates a load applied to a material when residual stress is measured, and includes a motor 111, a decelerator 112 and a ball screw 117.

A direct current (DC) stepping motor, which is stable against an external load and an overload and can be precisely controlled, is employed as the motor 111, thus eliminating influences of random factors which can be generated in a work area, such as external oscillation. The decelerator 112 is disposed below the motor 111 to decelerate the movement speed of the indenter 127 to the extent necessary for measurement of residual stress and amplify electric power outputted from the small-sized motor 111 when the indenter 127 is moved using electric power generated by the motor 111.

A coupling 113 is disposed below the decelerator 112 to couple the decelerator 112 and the ball screw 117 with each other and transfer electric power of the motor 111 to the ball screw 117. A bearing is fitted over the ball screw 117 to support the rotating movement of the ball screw 117.

Supporting shafts 116 penetrate through the body 102 to guide the movement of the body 102 when the body 102 moves upward and downward and prevent the shaking of the body 102 due to external impact or the shaking of the body 102 itself. The ball screw 117 rotates using electric power generated by the motor 111, and applies a load to the indenter 127 using rotary power generated during the rotation. A ball screw nut 118 is engaged with the ball screw 117 in a screw manner, so the ball screw nut 118 moves vertically when the ball screw 117 rotates.

The body 102 is pressed and combined with the ball screw nut 118 to convert rotary power supplied by the load applying device 110 according to the vertical movement of the ball screw nut 118 into a vertical load and enable the indenter 127 to apply the vertical load to a material. As described above, the supporting shafts 116 penetrate through the body 102.

The load sensor 123 is disposed below the body 102 to continuously measure the variation of the load applied by the body 102. If the load sensor 123 is indented, strain proportional to an indentation load is generated, and electrical resistance of a strain gauge contained in the load sensor 123 changes depending on the strain, thus varying current flowing through the load sensor 123. Accordingly, the load sensor 123 continuously measures the load by sensing the variation of the current.

The load sensor 123 is designed such that its maximum load is 100 kgf and its load resolution is 1.5 gf, so the maximum load thereof becomes smaller than that of a conventional Advance Indentation System (AIS) 2000, and the precision thereof becomes higher than that of the AIS 2000. The reason for this is that the AIS 2000 requires a larger load because a spherical indenter (not shown) must be used to obtain a tensile material property and the indenter must be pushed into a material more deeply than a predetermined depth, while the residual stress measuring apparatus can be designed as described above because the precision of equipment is considered to be prior to an indentation depth. In this case, as the maximum load increases, load resolution also increases to make precise analysis hard, while as the maximum load decreases, sufficient data cannot be obtained, and so an optimal load range is determined through various experiments.

An extension shaft 124 is disposed below the load sensor 123 to connect the load sensor 123 to the indenter 127. The extension shaft 124 has an internally threaded portion formed on an inner circumference of an upper end thereof and engaged with an externally threaded portion formed on a lower end of the load sensor 123.

The indenter 127 is disposed at the lower end portion of the extension shaft 124. The indenter 127 is a part for actually applying a contact load to a material. For example, in the shape of the indenter 127, a Vickers indenter is used as the indenter 127. The extension shaft 124 and the indenter 127 are designed to be detachable, so the indenter 127 is prevented from escaping from the extension shaft 124 and experimental errors are eliminated. In this embodiment, the indenter 127 is a Vickers indenter formed in the shape of a square pyramid, but it can be variously formed in the shape of a cone, square pyramid according to the use of the indenter 127.

The displacement sensor 128 moves in parallel with the indenter 127 and is disposed between the indenter 127 and the load sensor 123. The displacement sensor 128 measures displacement while moving in parallel with a magnet attached to an inner wall of the main body 100. A sensor bracket 129 is used to fasten the displacement sensor 128 to the extension shaft 124 connected to the indenter 127.

When the indenter 127 moves upward and downward, the displacement sensor 128 moves in parallel with the magnet to measure an insertion depth of the indenter 127, thus measuring an indentation depth of the indenter 127. A maximum measurement range of the displacement sensor 128 is a maximum movement range of the indenter 127. Further, in order to measure a precise indentation depth, a linear scale is used as the displacement sensor 128, but the displacement sensor 128 is not limited to the linear scale.

In order to prevent damage to the apparatus due to the compulsory up/down movement of both the indenter 127 and the displacement sensor 128, limit signal generating devices are attached to the top and bottom of the displacement sensor 128. That is, areas in which the indenter 127 and the displacement sensor 128 can stably move are set, and the limit signal generating devices are attached to limit positions of the areas. If the indenter 127 and the displacement sensor 128 deviate from the areas, the rotation of the motor ill is stopped, thus stopping the movement of both the indenter 127 and the displacement sensor 128.

The horizontal moving device 140 is disposed between the load applying device 140 and the load sensor 123, and a base 133. The horizontal moving device 140 is a device for performing a next residual stress measurement by horizontally moving only the frame 101 without moving the entire residual stress measuring apparatus, when next residual stress is measured at other positions of the same material after residual stress is measured at a previous position.

Referring to FIGS. 2 to 4, mainly, FIG. 4, the horizontal moving device 140, disposed below the frame 101 of the main body 100, is comprised of a slider 141, a slider base 142, a locker 143, a locking bolt 143a and a moving handle 145.

The slider 141 is placed below the frame 101 of the main body 100, and the slider base 142 is placed below the slider 141. A dovetail groove is formed in the slider base 142, and a dovetail protrusion is formed on the bottom of the slider 141, thus enabling the slider 141 and the slider base 142 to be slidably interlocked with each other using the dovetail groove and protrusion.

Therefore, the slider 141 slides on the slider base 142 in the direction of the dovetail groove and protrusion to horizontally move the main body 100. The locking bolts 143a pass through holes formed in the slider 141 to come into contact with a surface of the slider base 142. The locker 143 is interlocked with the locking bolt 143a, such that the locking bolt 143a moves upward and downward when the locker 143 is rotated. If the locker 143 is rotated to extend the locking bolt 143a, the locking bolt 143a pressurizes the slider base 142 to fasten the slider 141 to the slider base 142. At this time, if the locker 143 is rotated to shorten the locking bolt 143a, the locking bolt 143a depressurizes the slider base 142 and then allows the slider 141 to be horizontally movable when force is applied to the slider 141.

Force allowing the slider 141 to be horizontally movable is obtained by rotating the moving handle 145. The moving handle 145 is provided with a bolt 145, screwed into a nut 145c formed in the slider 141 while penetrating through a bracket 145a. When the moving handle 145 is rotated, the moving handle bolt 145b is also rotated. By the rotation of the moving handle bolt 145b, the moving handle nut 145c, the slider 141 and the frame 101 can move in the direction of the moving handle 145 or in the opposite direction thereof depending on the direction of the thread of the bolt 145b. On the moving handle 145, a scale is formed to allow a movement distance to be recognized.

The base 133 is disposed in the lower end of the main body 100. The base 133 is used to connect an attaching device 130 to the main body 100 and support the main body 100 when the attaching device 130 is not connected to the main body 100.

The residual stress measuring apparatus of the present invention has the attaching device 130 provided separately from the main body 100. The attaching device 130 includes a magnet 131, a magnet bracket 131a, and two bolts 133b and 133b'. The magnet 131 and the base 133 are screwed to the magnet bracket 131a through the two bolts 133b and 133b', respectively. The magnet 131 is used when an attached material is a ferrous material, and is used after the bottom of the magnet 131 is processed to correspond to a curvature in the case of a material with the curvature.

In this embodiment, although the attaching device 130 has been described as being the magnet 131, a chain or U-block with a curvature could be used as the attaching device 130 according to the type of materials to be attached. The chain is used such that it attaches a material to the main body 100 while surrounding the material, when the magnet 131 cannot be used. For example, a four-string chain is used to support a heavy load of approximately 100 kg, and a bolt engaging manner and a screw engaging manner for lockers are used together to lock the base 133 together with the chain. The U-block is used for a tube, wherein both side brackets supporting the main body 100 and the U-block are engaged through bolts to allow the tube to be fixed to the main body 100.

Referring to FIG. 1 again, the connectors 161 and 163 disposed on the upper portion of the frame 101 of the main body 100 are parts to transmit signals between the main body 100 and the interface computer 200. The connectors include the motor connector 161 and the signal connector 163, so they are connected to a motor connector 161' and a signal connector 163' of the interface computer 200, respectively.

The interface computer 200 is provided with a program for analyzing an indentation load and displacement data of a measured material to be able to calculate residual stress in a work area. Residual stress is calculated by a residual stress determining method using the measurement of residual stress, which will be described later.

Further, the program provided in the interface computer 200 has a function of manually driving the motor 111 to allow the indenter 127 to approach a material before the measurement of residual stress, or to remove the indenter 127 from the material after the measurement of residual stress, and an engaging function of automatically moving the indenter 127 to a position where the measurement of a material can be started when the measurement is started. These functions will be described later in detail.

The interface computer 200 includes the motor connector 161' and the signal connector 163' connected to the motor connector 161 and the signal connector 163 of the residual stress measuring apparatus, respectively. Further, the interface computer 200 is provided with predetermined control buttons, such as an emergency stop button, a power button or the like.

Hereinafter, the operation of the residual stress measuring apparatus of the present invention is described with reference to FIGS. 1 to 5.

After the attaching device 130 is connected to the base 133 of the main body 100, the attaching device 130 is attached to a material to be measured. When the locker 143 is not tightened, the locker 143 is rotated to move the locking bolt 143a downward, so the locking bolt 143a pressurizes the slider base 142 to allow the slider 141 and the main body 100 to be fastened to the slider base 142.

When the power button of the interface computer 200 is pressed to turn on power, the indenter 127 ascends as high as possible to reach a position where a limit signal is generated. An ascending speed at this time is a maximum speed at which the motor 111 and the decelerator 112 can ascend. A measurement speed and a manual up/down operating speed are changed by the decelerator 112 according to a preset rotation speed of the motor 111.

The rotatory force of the motor 111 rotates the decelerator 112 and the coupling 113 to rotate the ball screw 117, and vertically moves the ball screw nut 118 downward. The vertical movement of the ball screw nut 118 allows the body 102, the load sensor 123, the extension shaft 124, the indenter 127 and the displacement sensor 128 to simultaneously move downward.

At this time, the load sensor 123 and the displacement sensor 128 continuously measure the variations of a load and a displacement, respectively. The vertical load allows the indenter 127 to be pushed into the material. The displacement sensor 128 continuously measures an indentation depth by which the indenter 127 is pushed into the material. At one position, there is continuously carried out a process of obtaining stress and an actual contact area by measuring the load and the indentation depth to a certain extent through the load sensor 123 and the displacement sensor 128 and then measuring a load and an indentation depth while removing the load of the indenter 127 by some degree by rotating the motor 111 in the opposite direction.

Using the above method again, a load is applied to the indenter 127 to extend the indentation depth, thus measuring the load and the indentation depth and then continuously measuring the load and the indentation depth by removing the load again by some degree. As a result, stress and an actual contact area are obtained. By repeatedly carrying out this process, a stress versus strain curve at one position can be obtained.

After the indentation measurement has been completed at one position, the locker 143 of the horizontal moving device 140 is loosened and the moving handle 145 is rotated to horizontally move the slider 141. Thereafter, the indentation measurement is performed at the next position in the same manner as the above-described process.

In order to perform the measurement of residual stress for another material, the magnet 131 is detached from the attaching device 130, the entire residual stress measuring apparatus is moved to another material, and thereafter the magnet 131 is attached again to another material to perform residual stress measurement. Further, in order to attach the magnet 131 to a material with a curvature, the magnet 131 can be used after it is processed to be curved. On the other hand, if a measured material is not a magnetic substance, the bolts 133b and 133b', used to screw the base 133 to the magnet bracket 131a of the attaching device 130 in FIG. 5, are rotated to allow the attaching device 130 to be detached from the main body 100. After that, another attaching device 130, for example, a chain or U-block, is attached to the base 133 and then the measurement is performed in the same manner.

2. Residual Stress Data Measuring Method and Residual Stress Calculating Method Using Residual Stress Measuring Apparatus Mainly referring to FIGS. 6 to 8 and partially referring to FIGS. 1 to 5, embodiments of a residual stress data measuring method and residual stress calculating method using the residual stress measuring apparatus according to the present invention are described.

Figure 6:
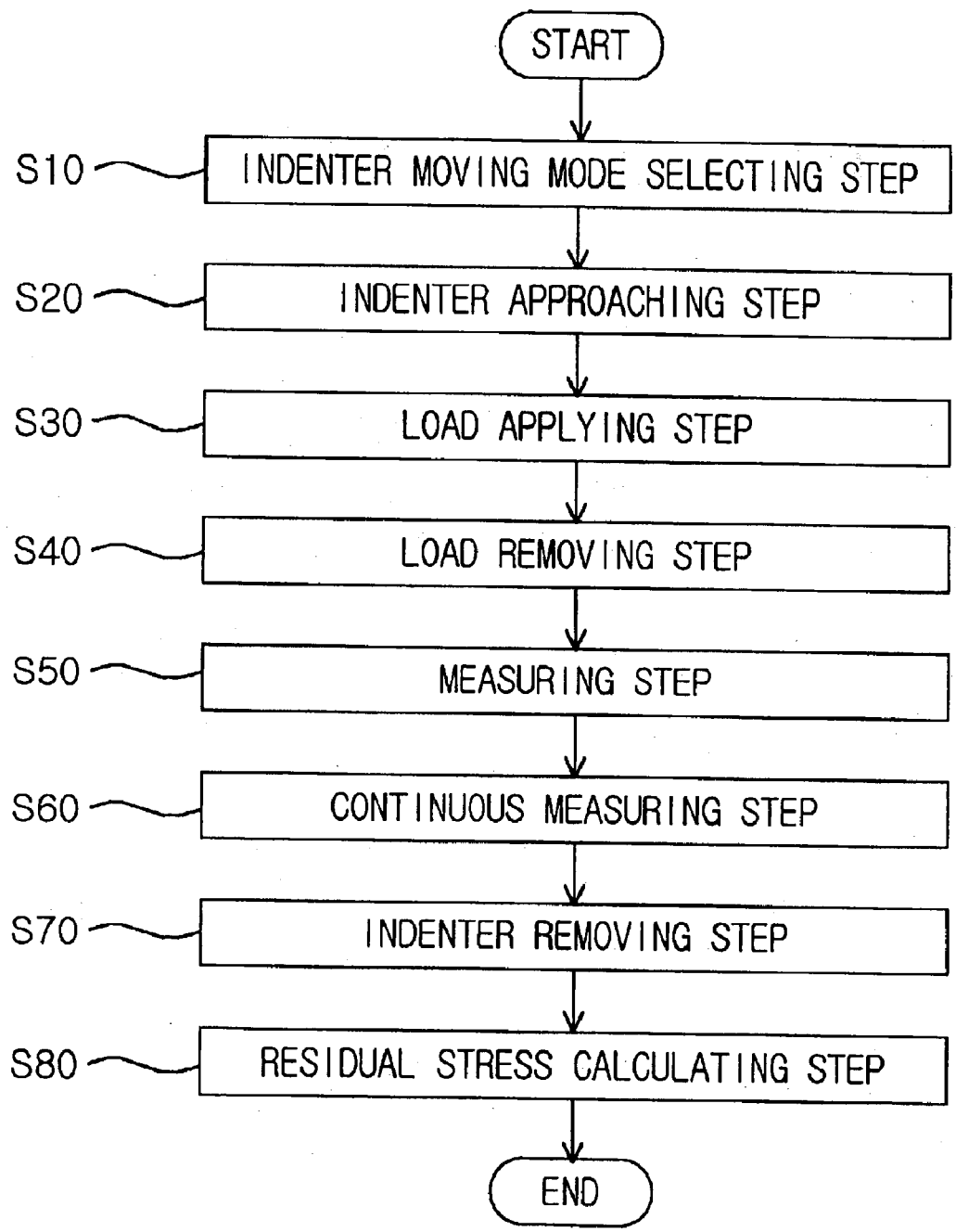
FIG. 6 is a flowchart of a method of measuring residual stress using the residual stress measuring apparatus according to an embodiment of the present invention.

As shown in FIG. 6, the residual stress measuring method using the residual stress measuring apparatus according to the present invention comprises an indenter moving mode selecting step S10, an indenter approaching step S20, a load applying step S30, a load removing step S40, a measuring step S50, a continuous measuring step S60, an indenter removing step S70, and a residual stress calculating step S80. In order to avoid repeated descriptions, the residual stress data measuring method is described together with the residual stress measuring method.

Figure 7:
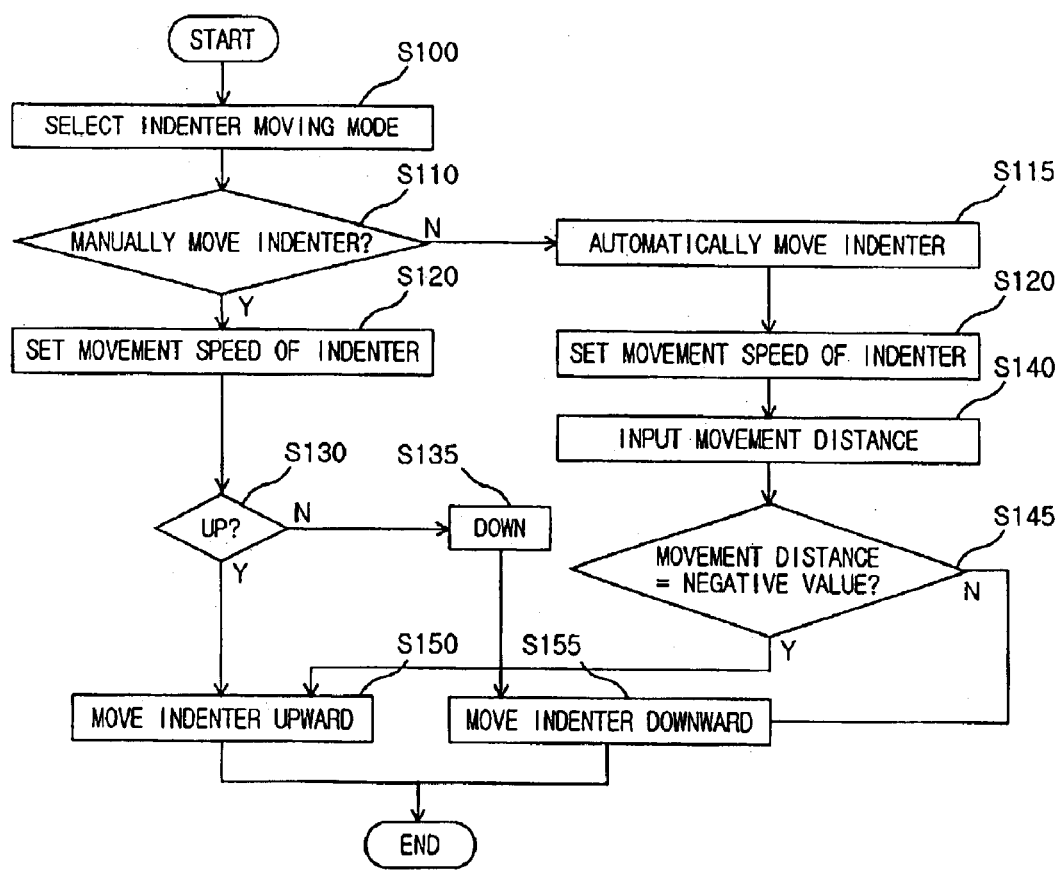
FIG. 7 is a detailed flowchart of an indenter moving mode selecting step of FIG. 6.

In the indenter moving mode selecting step S10, it is determined whether the indenter 127 of the residual stress measuring apparatus will be manually or automatically moved. Referring to FIG. 7, the moving mode of the indenter 127 is selected so as to allow the indenter 127 to approach a material before a measurement is started at step S100. It is determined whether the indenter 127 will be manually moved at step S110, and if it is determined that the indenter 127 will be manually moved, a movement speed of the indenter 127 is set at step S120. If the movement speed of the indenter 127 is set and then UP is selected at step S130, the indenter 127 moves upward at step S150. On the contrary, if DOWN is selected at step S135, the indenter 127 moves downward at step S155.

Even though it is determined that the indenter 127 will be moved automatically, not manually, at step S115, the movement speed of the indenter 127 must be set once at step S120'. Next, a movement distance is input at step S140, and it is determined whether the movement distance is a negative value at step S145. If the movement distance is a negative value, the indenter 127 is moved upward at step S150, while if the movement distance is a positive value, the indenter 127 is moved downward at step S155.

Figure 8:
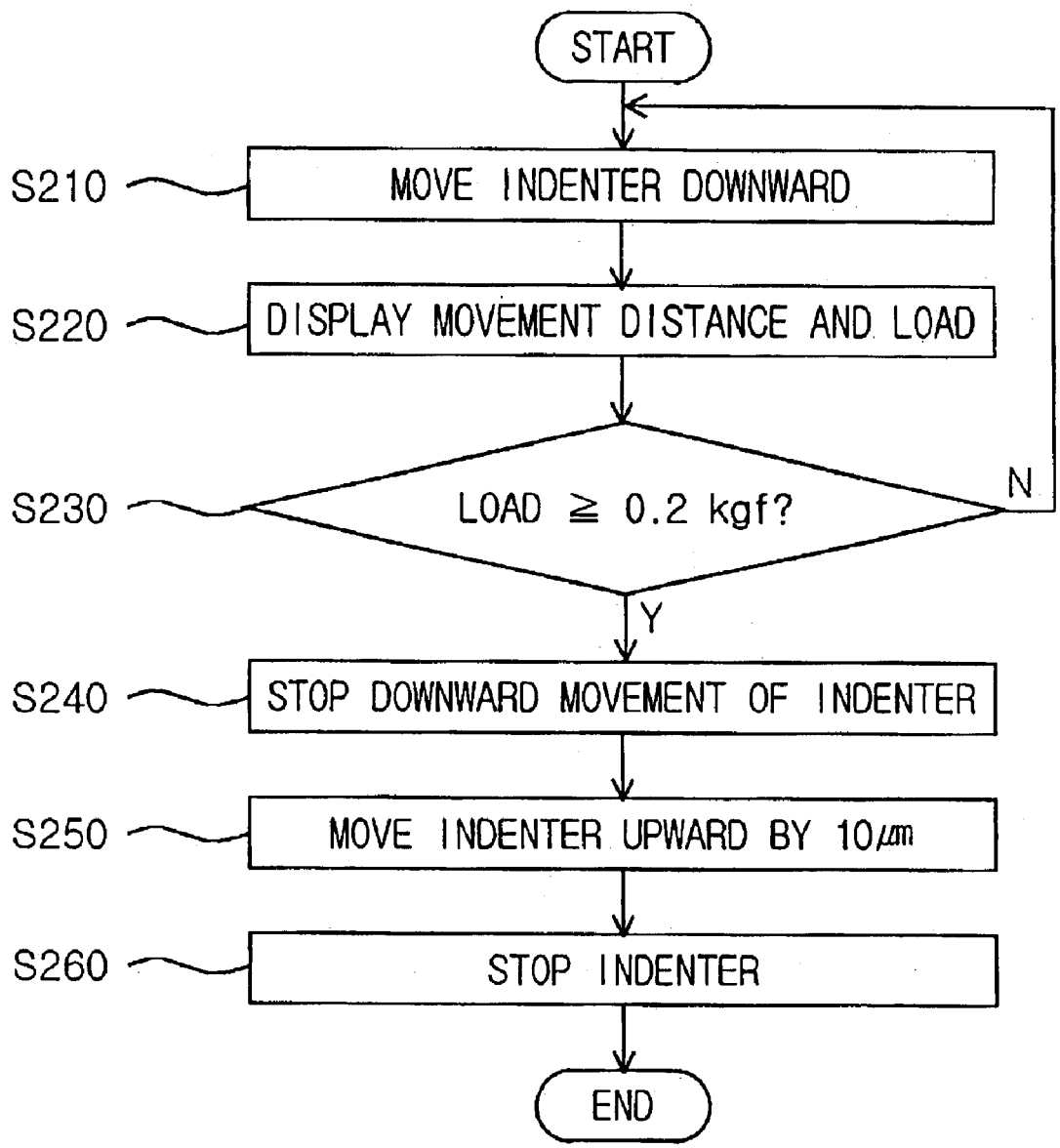
FIG. 8 is a detailed flowchart of an indenter approaching step of FIG. 6.

At the indenter approaching step S20, the indenter 127 moves to a position where the residual stress measurement can be started near the material. Referring to FIG. 8, a movement distance and a load are displayed in real time at step S220 while the indenter 127 moves downward at step S210. It is determined whether a load applied to the indenter 127 is greater than or equal to 0.2 kgf at step S230. If it is determined that the load is greater than or equal to 0.2 kgf, the indenter 127 stops its downward movement at step S240, moves upward by 10 $\mu$m at step S250, and then stops its movement at step S260.

In this way, a distance between the indenter 127 and the material is suitably set to such an extent that the measurement can be started. If the load is not greater than or equal to 0.2 kgf, the indenter approaching step is repeated while the indenter 127 continuously moves downward until the load of the indenter 127 reaches 0.2 kgf.

At this time, values 0.2 kgf and 10 μm represent a load set value and a distance set value, respectively, which are obtained through repeated experiments. A data measurement start range is above 0.2 kgf, so the set values do not influence the measurement of material properties. Further, in the embodiment, the load set value and the distance set value are 0.2 kgf and 10 μm, respectively; however, the load set value of engagement is valid within a range of 0.01 to 2 kgf and the distance set value thereof is valid within a range of 0.1 to 30 μm by the results of experiments. Accordingly, it is clear that the setting of the engagement within these ranges belongs to the scope of the present invention.

At the load applying step S30, a load is applied to the material to allow the indenter 127 to vertically descend. In this case, a vertical descending speed (movement speed) and a vertical descending length (movement distance) are preset. The movement speed and distance of the indenter 127 can be obtained by controlling both the motor 111 and the decelerator 112 of the residual stress measuring apparatus. For example, if a maximum movement distance (depth) is selected as 300 μm and the number of repetitions is selected as 10, the movement speed can be set to 0.1 mm/min, and the movement distance can be set to 30 μm for each time.

At the load removing step S40, the load is removed by a certain load removal ratio to allow the indenter 127 to move upward by a certain distance after the indenter 127 moves downward by the movement distance. This step can also be performed by controlling both the motor 111 and the decelerator 112 of the residual stress measuring apparatus. In the above example, if the load removal ratio is 30%, the indenter 127 moves upward to a load quantity corresponding to 70% of the load applied to obtain the movement distance for each time.

At the measuring step S50, an indentation depth and an indentation load of the indenter 127 according to the vertical movement of the indenter 127 are measured through the load applying step S30 and the load removing step S40. This step S50 is carried out by the displacement sensor 128 and the load sensor 123 of the residual stress measuring apparatus.

At the continuous measuring step S60, the load applying step S30, the load removing step S40 and the measuring step S50 are repeatedly performed a certain number of times. Meanwhile, the movement speed, the indenter movement distance, and the load removal ratio can be differently set according to the number of times. For example, if the number of times is small (1 to 3) and an applied load is small, the load removal ratio can be increased. Further, with the increase of the number of times, the load removal ratio can be decreased. If the number of times is small, the load removal ratio is increased, thus accurately reflecting the features of plastic strain.

At the indenter removing step S70, the indenter 127 is removed from the material.

At the residual stress measuring step S80, residual stress is calculated using an indentation load versus depth curve obtained using the measurements obtained at the measuring step S60. In this case, the residual stress can be calculated by a residual stress determining method using residual stress measurement, which will be described later. Properly, the residual stress calculating step S80 can be performed before or after the indenter removing step S70.

Hereinbefore, the residual stress data measuring method and the residual stress measuring method using the residual stress measuring apparatus are described with reference to the drawings, but the present invention is not limited to the above embodiments.

Since the above residual stress measuring method is repeatedly performed while horizontally moving the indenter 127 along one axial direction on the same material using the horizontal moving device 140 of the residual stress measuring apparatus, plural residual stress values can be calculated for the same material. In this case, data representing unnaturally small or large values among the plural measured residual stress values are discarded and the remaining residual stress values are averaged, such that residual stress of the material can be obtained more accurately.

3. Recording Medium for Storing Software of Residual Stress Measuring Method Using Residual Stress Measuring Apparatus Mainly referring to FIGS. 9 to 13 and partially referring to FIGS. 1 to 8, a recording medium for storing software of the residual stress measuring method using the residual stress measuring apparatus according to the present invention is described. The recording medium can be run by a computing device, such as a computer. For example, the recording medium is run by the computer including an interface capable of controlling the residual stress measuring apparatus shown in FIG. 1 to input measurement data of the residual stress measuring apparatus, and measure and output residual stress values of a material.

Figure 9:
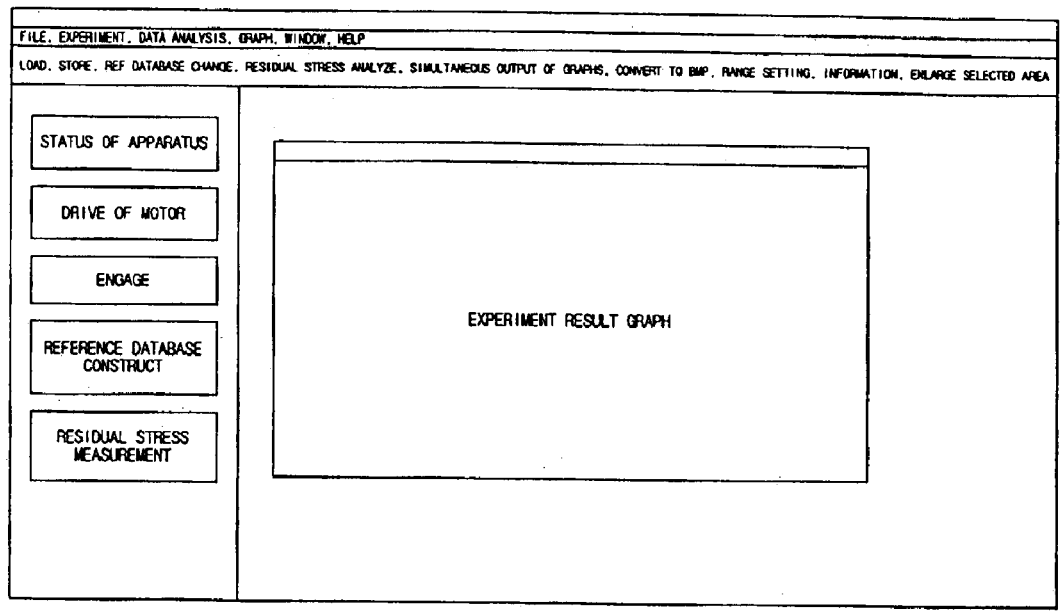
FIG. 9 is a view showing an initial screen when a recording medium for storing software of the measuring method using the residual stress measuring apparatus of FIG. 1 is run by the computer.
Figure 10:
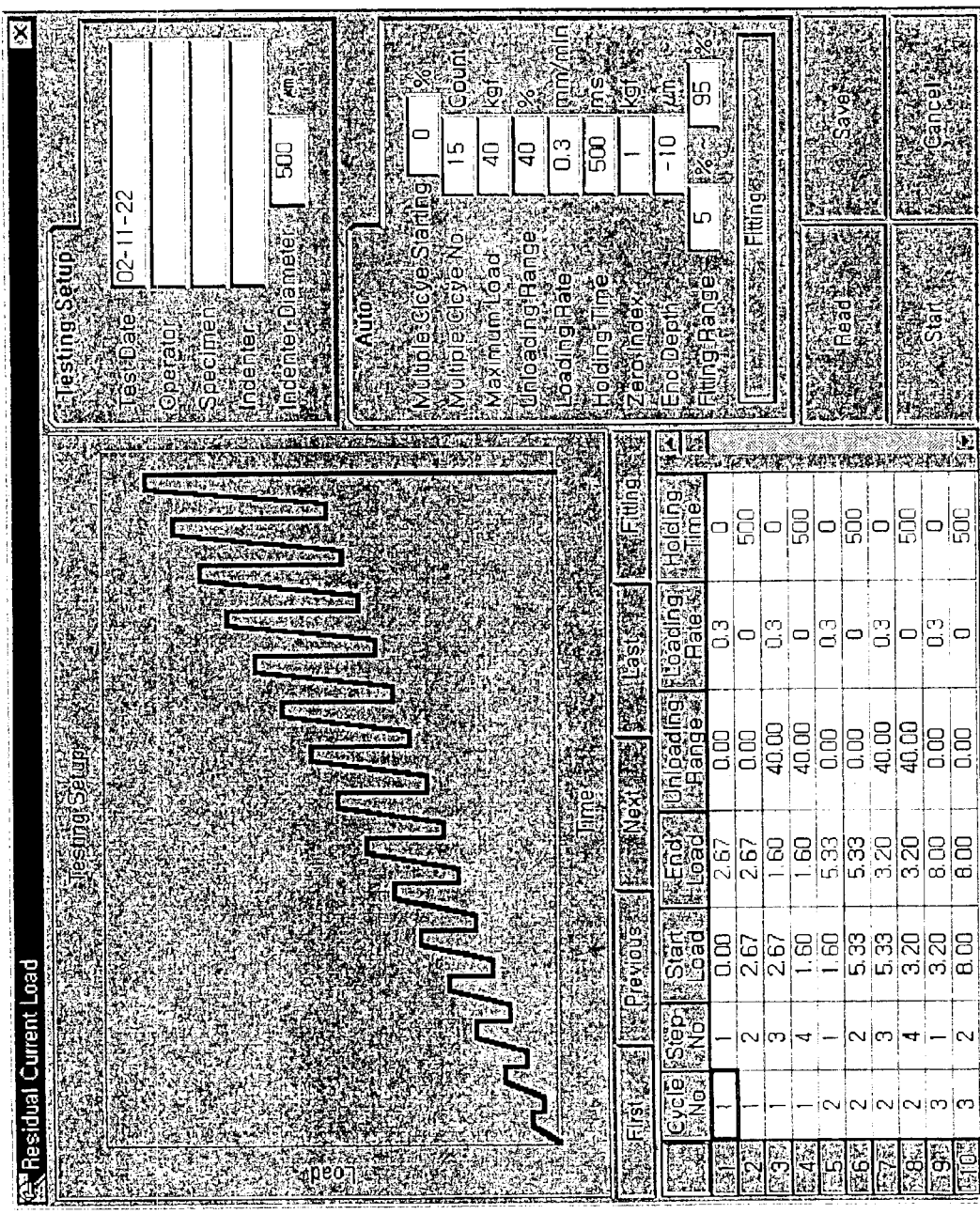
FIG. 10 is a view showing a screen on which experimental conditions are set.
Figure 11:
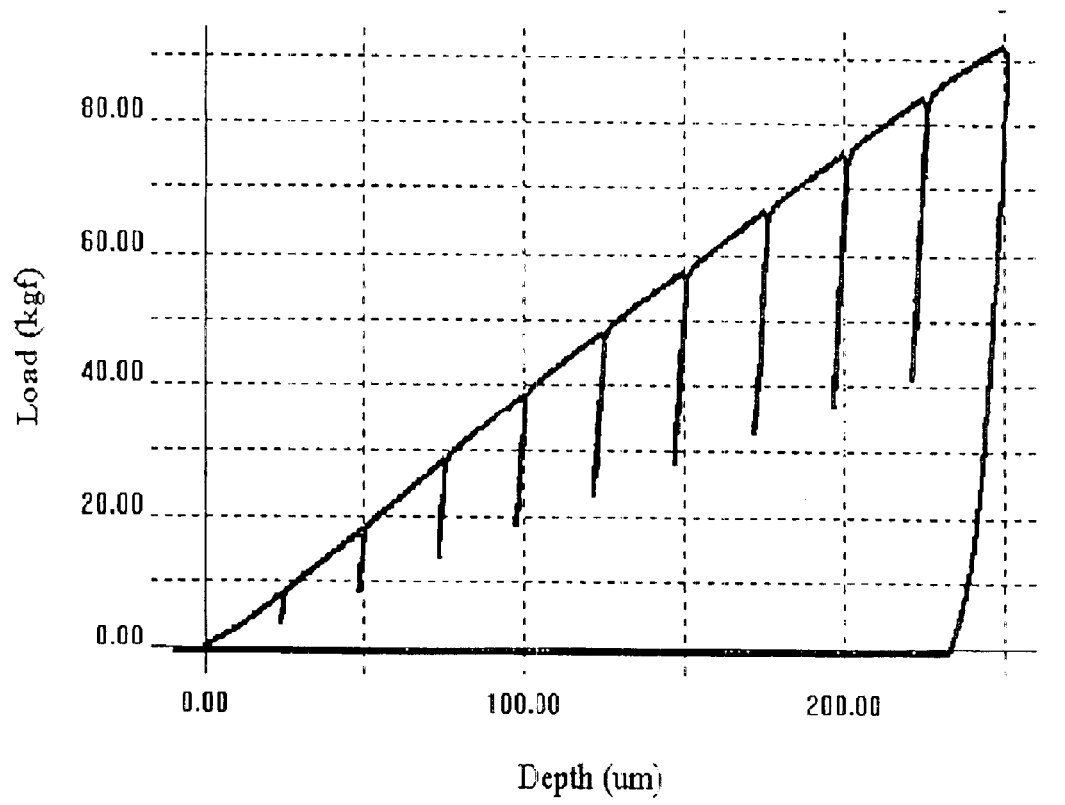
FIG. 11 is a graph showing an indentation load versus depth curve measured using the recording medium for storing software of the measuring method using the residual stress measuring apparatus of FIG. 1.
Figure 12:
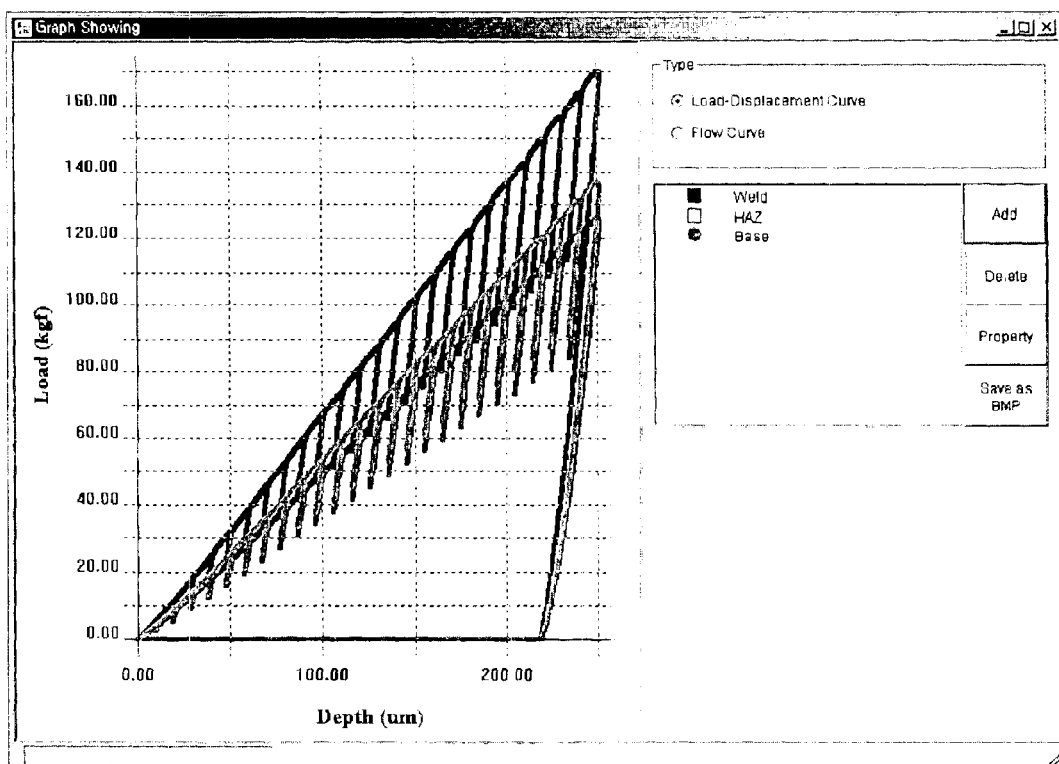
FIG. 12 is a graph showing results obtained by overlapping indentation load versus depth curves measured several times for the same material or different materials.
Figure 13:
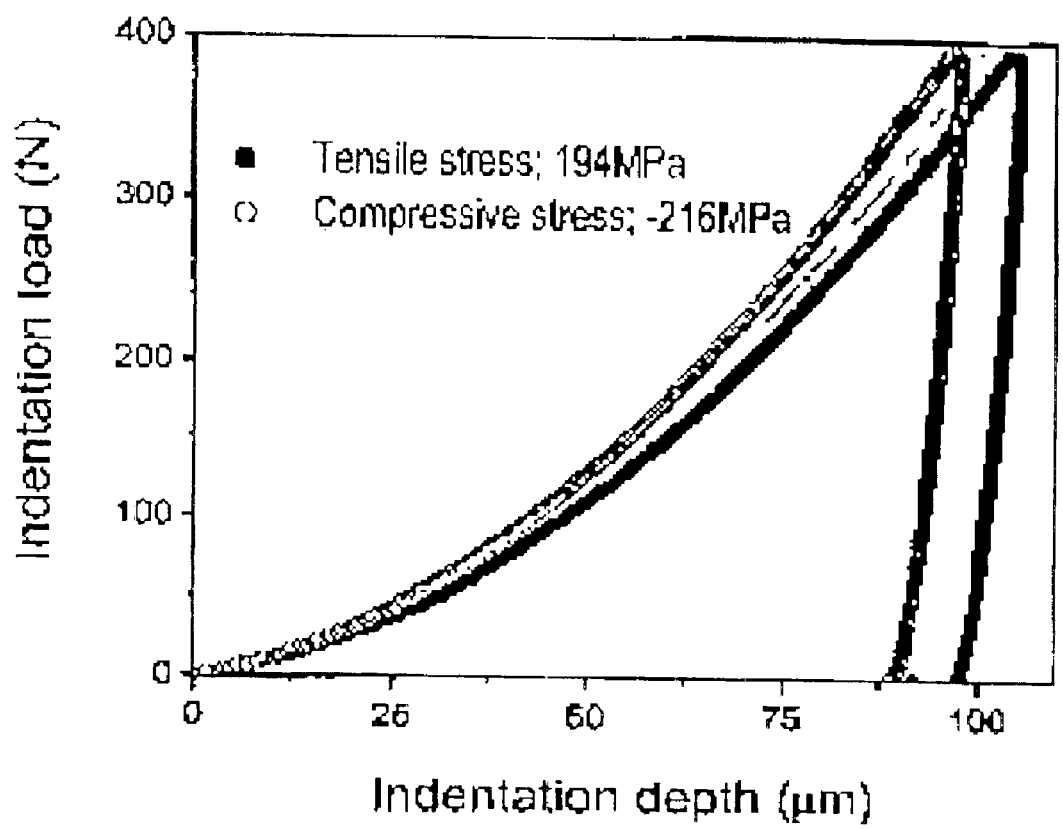
FIG. 13 is a graph showing analyzed results of residual stresses derived using the indentation load versus depth curve.

FIG. 9 is a view showing an initial screen when a recording medium for storing software of the measuring method using the residual stress measuring apparatus of FIG. 1 is run by the computer, FIG. 10 is a view showing a screen on which experimental conditions are set, FIG. 11 is a graph showing an indentation load versus depth curve measured using the recording medium for storing software of the measuring method using the residual stress measuring apparatus of FIG. 1, FIG. 12 is a graph showing results obtained by overlapping indentation load versus depth curves measured several times for the same material or different materials, and FIG. 13 is a graph showing analyzed results of residual stresses derived using the indentation load versus depth curve.

The initial screen displayed when the recording medium is run by the computer consists of a higher menu, a current apparatus status display field, a manual drive field for the motor 111, an engaging button, a graph window, a reference database construct button, and a residual stress experiment button. The menu items constituting the initial screen can be clicked using a mouse or keyboard, or can be manually manipulated using the keyboard.

The higher menu item includes basic menu items, such as load, store, reference database change and residual stress analyze. When the reference database construct button or residual stress measurement button is selected, information on an experimenter and a sample is input to a simple information input window and then the experimental condition setting screen is displayed. Experimental conditions include the type of indenter 127, the number of multiple experiments, maximum displacement, load removal ratio, load maintaining time and the like. The manual drive field arranged at the lower portion of the setting screen can be used to control a final displacement and a measurement speed. An experimental condition modeling view according to these experimental conditions is output to predict and output experimental results according to the experimental conditions.

The current apparatus status display field is used to display current load and displacement of the indenter 127 of the residual stress measuring apparatus. The manual drive field for the motor 111 is used to allow the indenter 127 to approach a material before residual stress is measured, or to remove the indenter 127 from the material so as to move to a next measurement position after the residual stress measurement is finished.

Referring to FIG. 7, if an UP button of the manual drive field is pressed after the movement speed of the indenter 127 is set, the indenter 127 moves upward. On the contrary, if a DOWN button thereof is pressed, the indenter 127 moves downward.

The engaging button is used to automatically move the indenter 127 to a position where the measurement of a material can be started so as to eliminate an experimenter's inconvenience of allowing the indenter 127 to approach the material while directly monitoring both the indenter 127 and the material when the indenter 127 moves to a position where the measurement of the material can be started. Referring to FIG. 8, when the engaging button is pressed, the indenter approaching step S20 of FIG. 6 is executed to move the indenter 127 to a measurable position.

When a start button (not shown) on the initial screen is pressed, the software of the measuring method stored in the recording medium is performed to enable a reference database for residual stress to be constructed, or residual stress to be measured.

As described above, the current load and displacement of the indenter 127 is displayed on the current apparatus status display field. Further, a curve of the indentation load versus indentation depth (displacement) accumulated up to now is displayed on the graph window, as shown in FIG. 11. When a plurality of indentation load versus depth curves are obtained while the indenter 127 horizontally moves on the same material, or when residual stress values vary according to measurement positions to require the comparison between the residual stress values, the curves can be overlapped and simultaneously displayed, as shown in FIG. 12.

On the initial screen, there are provided the reference database change button and the residual stress analyze button. Accordingly, if the reference database change button is clicked, a reference value can be selected among databases stored in equipment. If the residual stress analyze button is clicked, a residual stress analyze window is displayed on the screen to enable residual stress to be analyzed on the basis of the selected reference value. If an analysis start button is clicked, residual stress values are displayed. At the time of analyzing the residual stress values, a reference curve and a residual stress measurement curve are displayed, and analyzed results are also displayed on the screen together with the curves. These contents can be stored in various file formats, for example, image files such as BMP formats.

4. Embodiments of Residual Stress Measuring Method Using Measurement Program

Referring to FIGS. 11 to 14, in order to measure residual stress, an indentation load versus displacement curve of a reference sample (free from stress) is required. The reason for this is to compare an indentation load versus displacement curve of an actual sample with that of the reference sample. In order to measure residual stress, the following process must be executed, and the sequence thereof is described below.

First, continuous multiple indentation experiments for the reference sample are carried out using the above-described residual stress measuring apparatus. A fitting equation of a loading curve, a slope of an unloading curve, and an actual indentation depth $h_c$ are obtained on the basis of curves obtained from the experiments.

Only loading curves which are free from mechanical relaxation, deceleration/acceleration effect and creep effect are separated from the obtained indentation load versus displacement curves to execute a fitting process. This fitting process is required to measure a value more accurately, because sometimes the shapes of unloading curves are distorted a little in the case of actual multiple indentations and so the curves are slightly different from that of an actually applied load. A load applied when Vickers indentation experiments, indicating certain hardness, are carried out is proportional to an indentation area, but it is difficult to consider that the load is precisely proportional to the indentation area due to complicated elasticity/plastic strain under the indenter. Accordingly, a relation between the load and indentation depths given at the time of loading is fitted in the form of a fifth-order equation, as expressed in Equation [1], thus obtaining an experimental equation, $$L = a_1 h^5 + a_2 h^4 + a_3 h^3 + a_4 h^2 + a_5 h + c \quad [1]$$

wherein $a_1$, $a_2$, $a_3$, $a_4$, $a_5$, and c are constants.

Next, when each of unloading curves is analyzed, each unloading curve is also fitted in the form of the following Equation [2] in the same manner as the analysis of the loading curves. Equation [2] is an algorithm for calculating a curve closest to all points on the unloading curves, $$L = k(h - h_f)^m \quad [2]$$

where $h_f$ is a final residual depth after the load is removed. When logs are taken of both terms of Equation [2] to carry out a fitting process, k and m can be obtained, and the slope S of the unloading curve can be obtained through k and m. A relation between the slope S, and k and m is defined in the following Equation [3].

$$S = \left[\frac{dL}{dh}\right]_{h=h_{max}} = km(h - h_f)^{m-1} \quad [3]$$

A certain contact area between the indenter and the sample is maintained while an elastic indentation load is removed, the unloading curve is linear, and a contact depth $h_c$ is determined from the linear unloading curve. However, the contact area decreases depending on the actual shape of the indenter while the load is removed, and elastic bending around the contact area also varies. A relation indicating the contact between the indenter and the sample can be expressed as the following Equation [4].

In Equation [3], S is determined by taking a maximum displacement value on each unloading curve as $h_{max}$. After that, $h_{max}$ is re-set at an interacting The reason for this is to minimize error generated in the case where each unloading curve deviates from an ideal shape according to equipment clearance.

$$h_c = h_{max} - \omega(h_{max} - h_i) = h_{max} - \omega \frac{L_{max}}{S} \quad [4]$$

In Equation [4], $h_i$ is an intercept depth when the tangent line of the unloading curve is extended, and $h_{max}$ is a maximum indentation depth in each unloading curve, obtained using the intersection point between the above loading curve and the tangent line of the unloading curve, which can be obtained using the slope S.

ω is a geometric factor of the indenter and is given as 0.72 in the case of the Vickers indenter. Such contact depth determination is carried out for each unloading curve. For simplicity of description, the above equations are used in this embodiment; however there can be used a conventional method of determining a contact depth by taking a pile-up manner, in which materials are piled up on an indentation edge at the time of indentation, or sink-in manner, in which the materials are sunk in the indentation edge, into consideration. The conventional contact depth determining method is disclosed in a "Method of determining a processing hardenability index and a stress coefficient using continuous indentation experiments (Korean Pat. Appl. No. 10-2001-1770)", a "Method of determining a breakdown strength using continuous indentation experiments (Korean. Pat. Appl. No. 10-2001-1771)", and a "Method of determining a tensile strength using continuous indentation experiments (Korean. Pat. Appl. No. 10-2001-1772)", which were applied in 12 Jan., 2001 by the present applicant and are not opened yet.

After the experiments for the reference sample have been completed, experiments for samples requiring the measurement of residual stress are carried out. In this case, there is no need to perform a partial unloading step, which is due to the fact that, since a relative difference between applied loads with respect to a certain indentation depth at each sample is directly related to residual stress present in each sample, it is not necessary to obtain a value $h_c$ in the sample having residual stress after a standardized indentation depth $h_c$ has been previously obtained from the reference sample.

After continuous indentation experiments have been carried out for samples requiring the measurement of residual stress, a fitting procedure for a loading curve is executed in the same manner as the reference sample experiments. An equation obtained through the fitting procedure is compared with the fitting equation obtained from the reference sample. In this case, the sign of residual stress present in each sample can be determined through the shape of a measured indentation load versus displacement curve. That is, if the measured indentation load versus displacement curve is placed above that of the reference sample, it can be determined that compressive residual stress exists; otherwise it can be determined that tensile residual stress exists.

After loading curve equations are obtained, residual stress is measured by relations, which will be described later. It can be considered that a difference between indentation loads applied to the reference sample and an actual sample at the same indention depth is generated due to residual stress, so residual stress can be obtained by dividing the load difference by an actual contact area. In this embodiment, the load difference was obtained at the indentation depth $h_{max}$ obtained from each unloading curve. Therefore, several residual stress value can be evaluated from a single experiment using the multiple contact data for reference experiment.

A constant α exists because the distribution states of stresses present on the sample are different, for example, in the case of a equi-biaxial stress state ($\sigma_x=\sigma_y$) on a thin film, or in the case where only a single directional stress is considered to be important ($\sigma_x \gg \sigma_y$) like a welding part.

If the influence due to residual stress is indicated by a difference in an applied load at the same indentation depth, a stress value at this time can be expressed in the following Equation [5] because the stress value is obtained by dividing the applied load by a unit area, $$\sigma_{res} = \alpha \frac{L_{res}}{A_c}, \text{ where } L_{res} = L_0 - L_R \quad [5]$$

where $L_R$ is an indentation load applied to the actual sample, $L_0$ is an indentation load applied to the reference sample, and $A_c$ is an actual contact area and is expressed in the following Equation [6] in consideration of a geometric form of a Vickers indenter.

$$\text{where } A_c = 24.5 h_c^2 \quad [6]$$

If each value $A_c$ obtained by applying each $h_c$ obtained from the reference sample to Equation [6], is applied to Equation [5], actual residual stress values vary within a predetermined range, which is due to the fact that, as the indentation load increases, a plastic area under the indenter increases.

Accordingly, residual stress is defined by a mean value obtained by averaging residual stress values corresponding to contact areas.

As described above, the present invention provides an apparatus and method for measuring residual stress, which is advantageous for evaluation of a mechanical material property and is non-destructive.

The present invention is advantageous in that the residual stress measuring apparatus and method is widely applied to fields ranging from a microscopic area, such as a thin film or micro device, to a large-sized structure, and is not influenced by a microstructure by controlling the range of an applied load.

Further, the present invention is advantageous in that it is minimized in its volume to be easily attached to an actual structure.

Further, the present invention is advantageous in that various attaching devices are employed, thus enabling the apparatus to be attached to various materials regardless of the size and type of object materials to measure residual stress.

Further, the present invention is advantageous in that the residual stress measuring apparatus is horizontally movable, so there is no need to move an apparatus body itself so as to take measurements at several positions of several materials.

Further, the present invention is advantageous in that it does not require separate measurements for correcting experimental constants at the time of analyzing measured data, thus reducing measurement costs and enabling residual stresses of parts, which were impossible to measure using other conventional measuring methods, to be measured.

Further, the present invention is advantageous in that residual stress is directly evaluated in a non-destructive manner through the analysis of an indentation load versus displacement curve, thus preventing damage to samples, reducing time and costs required for measuring the samples, and enabling the residual stress measuring apparatus to be suitably applied even in the case where samples are difficult to obtain, or where local material property evaluation is required.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for measuring residual stress, comprising:
   a main body;

a load applying device installed within the main body to generate a load applied to a material to be measured;

a load sensor for continuously measuring variation of the load applied to the material by the load applying device;

an indenter holder connected to the load applying device and coaxially driven together with the load sensor;

an indenter provided with a first end coupled with the indenter holder and a second end coming into contact with the material to apply the load generated by the load applying device to the material;

a displacement sensor for continuously measuring variation of an indentation depth according to indentation of the indenter;

an interface computer provided with a measurement program for measuring residual stress on the basis of values measured by the load sensor and the displacement sensor;

an attaching device used to fix the material to be measured to the residual stress measuring apparatus, the attaching device being at least on of a magnet, a chain and a U-block; and a horizontal moving device for horizontally moving the main body with the indenter attached thereto in at least one direction after the attaching device is fixed to the residual stress measuring apparatus.

2. The residual stress measuring apparatus according to claim 1, wherein the horizontal moving device comprises:

a slider base connected to a base supporting the main body on an upper surface of the base and provided with a dovetail groove formed in an upper portion of the slider base;

a slider disposed between the slider base and the main body to be slidably interlocked with the slider base in a dovetail shape; and a moving handle for horizontally moving the slider on the slider base in at least one direction.

3. A method of measuring residual stress data of a material using a residual stress measuring apparatus, the apparatus comprising:

a main body;

a load applying device installed within the main body to generate a load applied to a material to be measured;

a load sensor for continuously measuring variation of the load applied to the material by the load applying device;

an indenter holder connected to the load applying device and coaxially driven together with the load sensor;

an indenter provided with a first end coupled with the indenter holder and a second end coming into contact with the material to apply the load generated by the load applying device to the material;

a displacement sensor for continuously measuring variation of an indentation depth according to indentation of the indenter; and an interface computer provided with a measurement program for measuring residual stress on the basis of values measured by the load sensor and the displacement sensor, the method of measuring comprising the steps of:

a) moving the indenter to a position where a residual stress experiment can be started to allow the indenter to approach the material;

b) setting a movement speed and a movement distance of the indenter and applying the load to the material;

c) vertically moving the indenter by the set movement depth of the indenter and then moving the indenter upward by a certain load removal ratio of the movement distance of the indenter;

d) measuring an indentation depth and an indentation load of the indenter according to the vertical movement of the indenter, simultaneously with performance of steps b) and c);

e) repeatedly performing the steps b), c) and d) a plurality of times;

f) removing the indenter from the material; and g) calculating residual stress of the material.

4. The residual stress data measuring method according to claim 3, wherein the step b) comprises the steps of:

b1) moving the indenter downward; and b2) stopping the downward movement of the indenter and moving the indenter upward by a distance set value if the indentation load is greater than or equal to a load set value, and continuously performing the step b1) if the indentation load is less than the load set value.

5. The residual stress data measuring method according to claim 4, wherein the load set value is 0.01 to 2 kgf, and the distance set value is 0.1 to 30 $\mu$m.

6. The residual stress data measuring method according to claim 3, wherein the step g) is performed before or after the step f) is executed.

7. The residual stress data measuring method according to claim 3, wherein the step e) is performed in such a way that at least one of the movement speed of the indenter, the movement distance of the indenter and the load removal ratio can be varied in each experiment step.

8. A method of measuring residual stress of a material using a residual stress measuring apparatus, the apparatus comprising:

a main body;

a load applying device installed within the main body to generate a load applied to a material to be measured;

a load sensor for continuously measuring variation of the load applied to the material by the load applying device;

an indenter holder connected to the load applying device and coaxially driven together with the load sensor;

an indenter provided with a first end coupled with the indenter holder and a second end coming into contact with the material to apply the load generated by the load applying device to the material;

a displacement sensor for continuously measuring variation of an indentation depth according to indentation of the indenter; and an interface computer provided with a measurement program for measuring residual stress on the basis of values measured by the load sensor and the displacement sensor, the method comprising the steps of:

a) moving the indenter downward to a position where an indentation experiment can be started, stopping the downward movement of the indenter and moving the indenter upward by a distance set value if an indentation load is greater than or equal to a load set value, and continuously moving the indenter downward, if the indentation load is less than the load set value;

b) setting a movement speed and a movement distance of the indenter and applying the load to the material;

c) vertically moving the indenter downward by the set movement distance of the indenter and then moving the indenter upward by a certain load removal ratio of the movement distance of the indenter;

d) measuring an indentation depth and an indentation load of the indenter according to the vertical movement of the indenter through the steps b) and c);

e) repeatedly performing the steps b), c) and d) a plurality of times;

f) measuring residual stress of the material by comparing measurement equations of a reference sample and the measured material with each other; and g) removing the indenter from the material.

9. A recording medium for storing software of a method of measuring residual stress of a material using a residual stress measuring apparatus, the apparatus comprising:

a main body;

a load applying device installed within the main body to generate a load applied to a material to be measured;

a load sensor for continuously measuring variation of the load applied to the material by the load applying device;

an indenter holder connected to the load applying device and coaxially driven together with the load sensor;

an indenter provided with a first end coupled with the indenter holder and a second end coming into contact with the material to apply the load generated by the load applying device to the material;

a displacement sensor for continuously measuring variation of an indentation depth according to indentation of the indenter; and an interface computer provided with a measurement program for measuring residual stress on the basis of values measured by the load sensor and the displacement sensor, the recording medium comprising:

indenter approaching means for moving the indenter downward to a position where an indentation experiment can be started, stopping the downward movement of the indenter and moving the indenter upward by a distance set value if an indentation load is greater than or equal to a load set value, and continuously moving the indenter downward if the indentation load is less than the load set value;

load applying means for setting a movement speed and a movement distance of the indenter and applying the load to the material;

load removing means for vertically moving the indenter down by the set movement distance of the indenter and then moving the indenter upward by a certain load removal ratio of the movement distance of the indenter;

measuring means for measuring an indentation depth and an indentation load of the indenter according to the vertical movement of the indenter through the load applying means and the load removing means;

continuous measuring means for repeatedly performing operations of the load applying means, the load removing means and the measuring means a plurality of times;

indenter removing means for removing the indenter from the material; and means for measuring residual stress of the material by comparing measurement equations of a reference sample and the measured material with each other.

10. An apparatus for measuring residual stress with a main body and a load applying device installed within the main body to generate a load applied to a material to be measured, comprising:

a load sensor for continuously measuring variation of the load applied to the material by the load applying device;

an indenter holder connected to the load applying device and coaxially driven together with the load sensor;

an indenter provided with a first end coupled with the indenter holder and a second end coming into contact with the material to apply the load generated by the load applying device to the material;

a displacement sensor for continuously measuring variation of an indentation depth according to indentation of the indenter;

an interface computer provided with a measurement program for measuring residual stress on the basis of values measured by the load sensor and the displacement sensor and with one or more control buttons for controlling the load applying device;

an attaching device used to fix the material to be measured to the residual stress measuring apparatus, the attaching device being at least one of a magnet, a chain and a U-block; and a horizontal moving device for horizontally moving the main body with the indenter attached thereto in at least one direction after the attaching device is fixed to the residual stress measuring apparatus; and wherein the measurement program measures the variations of the load and the indentation depth by allowing the indenter to approach the material to apply the load to the material by an operation of any one of the control buttons and removing the applied load, and further calculates residual stress by continuously measuring the variations of the load and the indentation depth.

11. The residual stress measuring apparatus according to claim 10, wherein the horizontal moving device comprises:

a slider base connected to a base supporting the main body on an upper surface of the base and provided with a dovetail groove formed in an upper portion of the slider base;

a slider disposed between the slider base and the main body to be slidably interlocked with the slider base in a dovetail shape; and a moving handle for horizontally moving the slider on the slider base in at least one direction.

12. The residual stress measuring apparatus according to claim 10, wherein the indenter is formed in at least one shape of a sphere, a cone and a square pyramid, and is integrated with the indenter holder.

13. The residual stress measuring apparatus according to claim 11, wherein the indenter is formed in at least one shape of a sphere, a cone and a square pyramid, and is integrated with the indenter holder.

14. A method of measuring residual stress data of a material using the residual stress measuring apparatus of claim 10, comprising the steps of:

a) moving the indenter to a position where a residual stress experiment can be started to allow the indenter to approach the material;

b) setting a movement speed and a movement distance of the indenter and applying the load to the material;

c) vertically moving the indenter by the set movement depth of the indenter and then moving the indenter upward by a certain load removal ratio of the movement distance of the indenter;

d) measuring an indentation depth and an indentation load of the indenter according to the vertical movement of the indenter, simultaneously with performance of steps b) and C);

e) repeatedly performing the steps b), c) and d) a plurality of times;

f) removing the indenter from the material; and g) calculating residual stress of the material.

15. The residual stress data measuring method according to claim 14, wherein the step b) comprises the steps of:

b1) moving the indenter downward; and b2) stopping the downward movement of the indenter and moving the indenter upward by a distance set value if the indentation load is greater than or equal to a load set value, and continuously performing the step b1) if the indentation load is less than the load set value.

16. The residual stress data measuring method according to claim 15, wherein the load set value is 0.01 to 2 kgf, and the distance set value is 0.1 to 30 µm.

17. The residual stress data measuring method according to claim 14, wherein the step g) is performed before or after the step f) is executed.

18. The residual stress data measuring method according to claim 14, wherein the step e) is performed in such a way that at least one of the movement speed of the indenter, the movement distance of the indenter and the load removal ratio can be varied in each experiment step.

* * * * *